(12) United States Patent
Shrubsole et al.

(10) Patent No.: US 11,147,494 B2
(45) Date of Patent: Oct. 19, 2021

(54) WEARABLE BIOPOTENTIAL PATCH WITH METHOD TO OPTIMIZE COMFORT AND ACCURACY

(71) Applicant: KONINKLIJKE PHILIPS N.V., Eindhoven (NL)

(72) Inventors: Paul Anthony Shrubsole, Arnhem (NL); Elise Claude Valentine Talgorn, Eindhoven (NL); Nicolaas Petrus Willard, Valkenswaard (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 128 days.

(21) Appl. No.: 16/518,490

(22) Filed: Jul. 22, 2019

(65) Prior Publication Data
US 2021/0022632 A1  Jan. 28, 2021

(51) Int. Cl.
| | |
|---|---|
| *A61B 5/318* | (2021.01) |
| *A61B 5/0533* | (2021.01) |
| *A61B 5/145* | (2006.01) |
| *A61B 5/1491* | (2006.01) |
| *A61B 5/00* | (2006.01) |
| *A61B 5/398* | (2021.01) |
| *A61B 5/369* | (2021.01) |
| *A61B 5/389* | (2021.01) |
| *A61B 5/01* | (2006.01) |

(52) U.S. Cl.
CPC ............ *A61B 5/318* (2021.01); *A61B 5/0533* (2013.01); *A61B 5/1491* (2013.01); *A61B 5/14521* (2013.01); *A61B 5/6833* (2013.01); *A61B 5/01* (2013.01); *A61B 5/369* (2021.01); *A61B 5/389* (2021.01); *A61B 5/398* (2021.01); *A61B 5/4266* (2013.01); *A61B 5/486* (2013.01); *A61B 2562/18* (2013.01)

(58) Field of Classification Search
CPC ......... A61B 5/01; A61B 5/1491; A61B 5/318; A61B 5/332; A61B 5/333; A61B 5/6823; A61B 5/6833
See application file for complete search history.

(56) References Cited

U.S. PATENT DOCUMENTS

| | | | |
|---|---|---|---|
| 4,266,556 A | 5/1981 | Barlow et al. | |
| 6,138,044 A * | 10/2000 | Svedman | ............... A61B 5/252 600/387 |
| 2012/0078071 A1 * | 3/2012 | Bohm | ................ A61B 5/14532 600/345 |

(Continued)

OTHER PUBLICATIONS

International Search Report and Written Opinion, International Application No. PCT/EP2020/070617, dated Jan. 18, 2021.

*Primary Examiner* — Allen Porter (57) ABSTRACT

The described embodiments relate to a self-regulating patch for taking biopotential measurements and balancing accurate measurements and user comfort. The self-regulating patch including: a heating element operable to generate heat that causes formation of sweat at the skin surface; a biopotential sensor; an exterior surface constructed of a moisture wicking material enveloping the heating element; and a logic to concurrently activate the biopotential sensor and transition the self-regulating patch between a plurality of modes, including a comfort mode and an accuracy mode, where in the comfort mode the heating element is inactive and in the accuracy mode the heating element is active.

20 Claims, 4 Drawing Sheets

(56) References Cited

U.S. PATENT DOCUMENTS

| | | |
|---|---|---|
| 2014/0031705 A1 | 1/2014 | Kurzweil et al. |
| 2014/0100436 A1 | 4/2014 | Brunner et al. |
| 2014/0343392 A1 | 11/2014 | Yang |
| 2016/0374598 A1 | 12/2016 | Heikenfeld et al. |
| 2017/0099539 A1* | 4/2017 | Di Censo .............. H04R 1/1008 |
| 2017/0304651 A1 | 10/2017 | Takayanagi et al. |
| 2018/0271393 A1* | 9/2018 | Lee ........................ A61B 5/296 |
| 2021/0000417 A1* | 1/2021 | Varadan ............... A61B 5/1486 |

* cited by examiner

WEARABLE BIOPOTENTIAL PATCH WITH METHOD TO OPTIMIZE COMFORT AND ACCURACY

TECHNICAL FIELD

Embodiments described herein are directed generally to wearable skin patches. More particularly, but not exclusively, the various systems, methods, and apparatus disclosed herein relate to a wearable biopotential measurement patch that is self-regulating in order to maintain both wearer comfort and measurement accuracy.

BACKGROUND

Wearable skin patches have become increasingly common, and may be utilized for various application such as sports, drug-delivery, or patient monitoring. Part of the increase in the use of skin patches may be attributed to factors such as their ability to be hidden under clothing and that they may not interfere with a wearer's movement, and therefore the wearer may be able to record more accurate data over a continuous and prolonged period of time. Conventionally, the wearable patches, devices, or the like, face at least four challenges: 1) battery efficiency; 2) accuracy; 3) adhesion; and, 4) comfort.

Biopotential sensor patches provide continuous measurements of the electrical activity generated by various physiological processes. One example biopotential is Electrocardiogram ("ECG"), which is measured electrical activity of the heart. ECG sensor patches may be especially desirable, for example, with heart failure patients who may be at risk for adverse events following discharge from hospital, although there are numerous other situations when such sensor patches may be desirable. The electrodes of conventional ECG patches fall into one of two categories of electrode: those that use a wet electrode and those that use a dry electrode. Wet electrodes use a gel to reduce contact impedance between the skin and the electrode by making the outer layer of skin ion conductive; however, due to the dehydration of the gel, these electrodes can be used for only short periods of time. Furthermore, the gel may cause skin irritations and support bacterial growth. Dry electrodes are conventionally used for long-term monitoring (e.g. in a clinical care setting or at home) because they may not result in the same degree of skin irritation demonstrated by gel-based solutions. However, even with a dry electrode, the metal of the electrode may still require some moisture to electrically couple with biopotentials generated by physiological processes occurring within the body. Performance of dry electrodes may increase when more moisture permeates the skin-electrode interface, which is important for reducing contact impedance.

As such, a need exists for a self-regulating patch, for example a patch that may be capable of raising hydration levels at the skin while a biopotential measurement is taken, but subsequently allowing for moisture to be removed or released from the skin surface when biopotential measurements are not being taken in order to minimize wearer discomfort and skin maceration.

SUMMARY

The present disclosure is directed to systems, methods, and apparatus for using a self-regulating patch for adhering to a skin surface. This patch may, in some embodiments, include: a heating element that is operable to generate heat, where the heat causes formation of sweat at the skin surface; an electrocardiogram ("ECG") sensor; an exterior surface enveloping the heating element and the ECG sensor, where the exterior surface is constructed of a material that draws moisture away from the ECG sensor; a logic to concurrently; activate the ECG sensor; and transition the self-regulating patch between a plurality of modes, including a comfort mode and an accuracy mode; where in the comfort mode the heating element is inactive, and where in the accuracy mode the heating element is active.

In some embodiments, the logic further concurrently utilizes one or more properties of an ECG signal generated by the ECG sensor to infer a moisture level on the skin surface. In some embodiments, the logic transitions the self-regulating patch between the comfort mode and the accuracy mode based on the inferred moisture level. In other embodiments, the one or more properties of the ECG signal include a signal-to-noise ratio. In still other embodiments, the accuracy mode comprises a feedback mode, where the heating element is further operable to generate heat in increments, and where the logic operates the heating element to generate a selected increment of heat, where the increment of heat is selected based on the inferred moisture level.

In some embodiments, the heating element comprises a metallic mesh disposed adjacent an electrode of the ECG sensor. In other embodiments, the heating element comprises a metallic wire disposed on an electrode of the ECG sensor. In some embodiments, the further includes a moisture sensor to facilitate the transition between the plurality of heating modes. In other embodiments, the patch further includes a drying material disposed adjacent an electrode of the ECG sensor. In still other embodiments, the heating element reaches a temperature between about 38 degrees Celsius and about 42 degrees Celsius at the skin surface when active.

In another aspect, another embodiment of a self-regulating patch for adhering to a skin surface is described herein, including: a heating element operable to generate heat in increments, where the heat causes formation of sweat at the skin surface; an electrocardiogram ("ECG") sensor; an exterior surface enveloping the heating element and the ECG sensor, where the exterior surface is constructed of a material that draws moisture away from the ECG sensor; a logic to: activate the ECG sensor; utilize one or more properties of an ECG signal generated by the ECG sensor to infer a moisture level on the skin surface; determine a selected increment of heat based on the inferred moisture level; and operate the heating element to generate the selected increment of heat.

In yet another aspect, a method of regulating a biopotential skin patch adhered to a skin surface of a subject in order to balance comfort and moisture levels is disclosed herein, where the biopotential skin patch comprises a heating element operable to generate heat in increments to cause formation of sweat at the skin surface, a biopotential sensor, an exterior surface that draws moisture away from the biopotential sensor and that envelops the heating element and the biopotential sensor, and a logic operably coupled with the heating element and the biopotential sensor, the method including: activating, by the logic, the biopotential sensor to measure electrical activity generated by one or more physiological processes of the subject; inferring, by the logic, a moisture level based on one or more properties of a signal generated by the biopotential sensor; determining a selected increment of heat based on the inferred moisture level; operating, by the logic, the heating element to generate the selected increment of heat.

In some embodiments, the heating element takes the form of a metallic mesh positioned against an electrode of the biopotential sensor. In other embodiments, the one or more properties of the signal generated by the biopotential sensor includes a signal-to-noise ratio. In still other embodiments, the heating element takes the form of a metallic wire positioned adjacent an electrode of the biopotential sensor.

The term "controller" is used herein generally to describe various apparatus relating to the implementations discussed herein. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In one network implementation, one or more devices coupled to a network may serve as a controller for one or more other devices coupled to the network (e.g., in a master/slave relationship). In another implementation, a networked environment may include one or more dedicated controllers that are configured to control one or more of the devices coupled to the network. Generally, multiple devices coupled to the network each may have access to data that is present on the communications medium or media; however, a given device may be "addressable" in that it is configured to selectively exchange data with (i.e., receive data from and/or transmit data to) the network, based, for example, on one or more particular identifiers (e.g., "addresses") assigned to it.

The term "network" as used herein refers to any interconnection of two or more devices (including controllers or processors) that facilitates the transport of information (e.g., for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The described embodiments relate to a self-regulating patches for attaching to a skin surface of a subject's body. As described in further detail herein, some aspects of the self-regulating patch include multiple heating modes in order to raise the moisture level at a skin surface of a subject (also referred to herein alternatively as a "wearer" or a "user") through locally induced sweating when biopotential measurements are to be taken, while also allowing the release of moisture when no biopotential measurements are being taken in order to improve a user's comfort.

Figure 1:
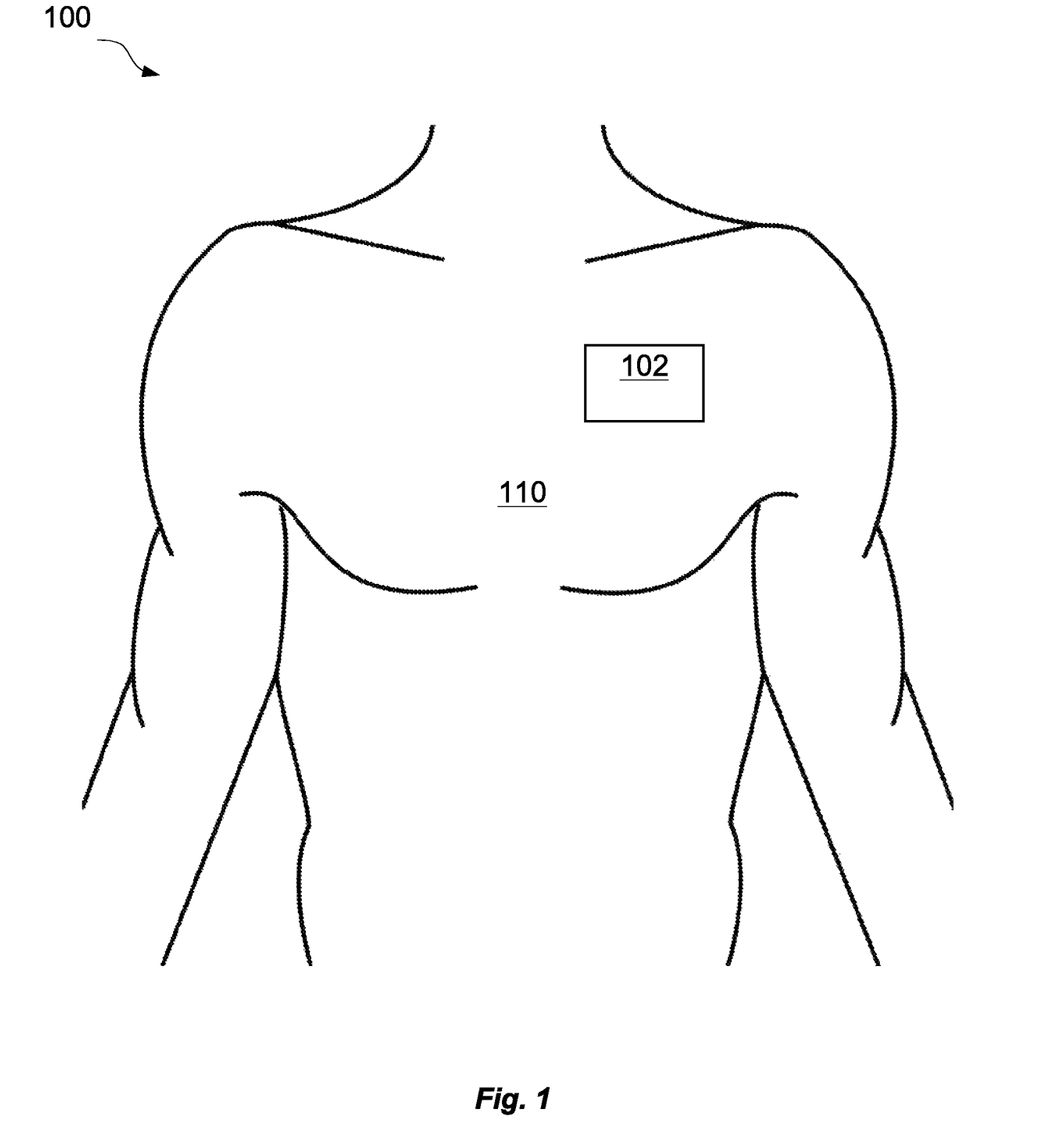
FIG. 1 illustrates an embodiment of a self-regulating patch that is adhered to a chest of a user.

FIG. 1 illustrates a perspective view 100 of an embodiment of a self-regulating patch 102 adhered to a chest 110. The self-regulating patch 102 may include a biopotential sensor (not depicted) for taking measurements of the electrical activity generated by various physiological processes. In examples described herein, the biopotential will be described primarily as an ECG sensor for taking ECG readings or measurements of the electrical activity of the heartbeat. However, this is not meant to be limiting; other types of biopotential sensors are contemplated herein, including but not limited to electroencephalography (EEG) for measuring the brain's electric activity from the scalp, electromyography (EMG) for measuring the electric activity of active muscle fibers, and electrooculography (EOG) for measuring electric potentials created as a result of the movement of the eyeballs.

ECGs work such that with each heartbeat, an electrical impulse (or "wave") travels through the heart, this wave causes the heart muscle to squeeze and pump blood from the heart. Generally, ECGs may provide two types of information. First, by measuring time intervals on an ECG reading, a physician may be able determine how long the electrical wave takes to pass through the heart, which allows for a determination of if the electrical activity is normal, slow, fast, and/or irregular. Second, by measuring the amount of electrical activity passing through the heart muscle, a physician may be able to determine if parts of the heart are too large and/or overworked. Although illustrated on the forearm of a user, this is not intended to be limiting, as the placement shown is merely illustrative as the patch may be placed on any skin surface practical for taking an ECG measurement.

The self-regulating patch 102 may also include a heating element, power source, exterior surface, and/or a logic for controlling the ECG sensor and heating element of the self-regulating patch 102. By way of example, a logic may be a computing element, such as a processor, a microprocessor, a processing element or unit, and/or the like, that is capable of executing logic. A logic may include an input/output element and a power or energy source. In some embodiments, the self-regulating patch 102 may include a transmitter for transmitting the measured ECG data. The logic, transmitter, and/or power source may be located in and/or on the self-regulating patch 102 (e.g., within the exterior surface of the self-regulating patch 102) and/or in remote location from the patch 102. In some embodiments, the operating electronics may be an application specific integrated circuit (ASIC). Although this should not be understood to be limiting, as in other instances the operating electronics may be a simple analog circuit or a field programmable gate array (FPGA).

Figure 2:
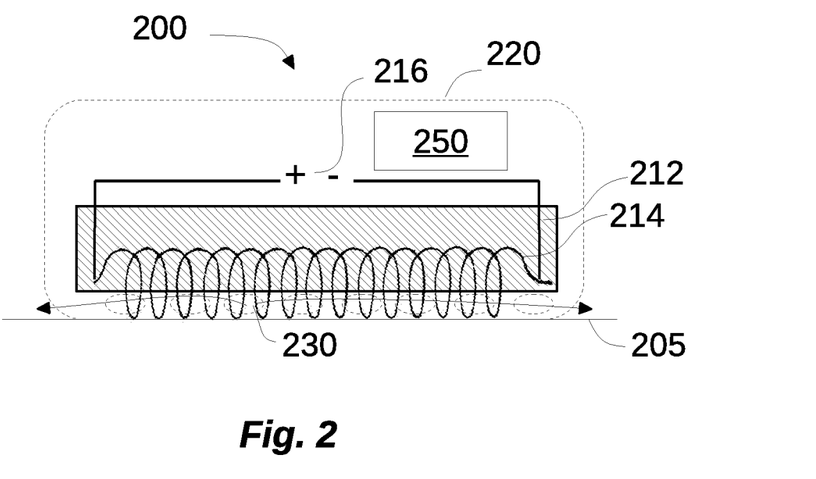
FIG. 2 illustrates a cross-sectional view of a self-regulating patch that is adhered to a user's skin surface according to some embodiments.
Figure 3:
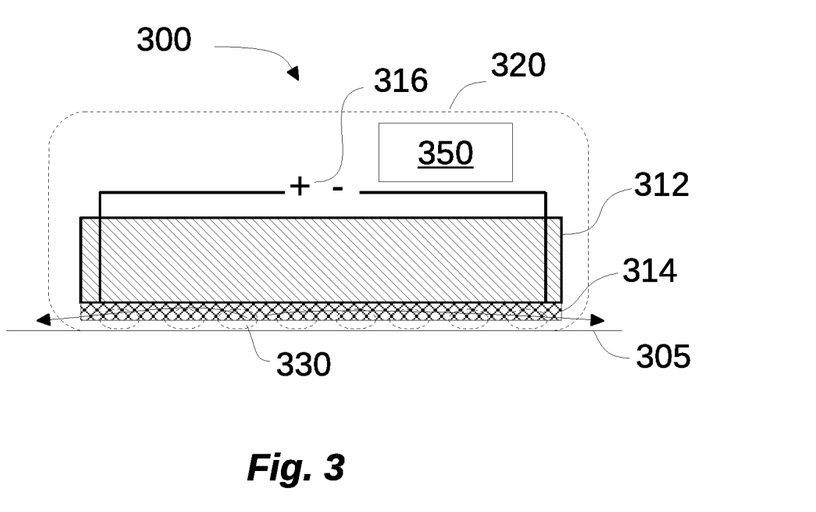
FIG. 3 illustrates a cross-sectional view of a self-regulating patch that is adhered to a user's skin surface according to some embodiments.

FIGS. 2 and 3 illustrate cross-sectional views of self-regulating patches 200, 300. Each of the self-regulating patches 200, 300 are illustrated as being positioned against a user's skin surface 205, 305. Each patch 200, 300 may include an exterior surface 220, 320 that envelops a heating element 214, 314 (described in detail below), an ECG electrode 212, 312, and a logic 250, 350. In some instances, the exterior surface 220, 320 may be constructed of a porous or water permeable material (represented by broken line in FIGS. 2 and 3) that draws moisture away from the electrode 212, 312, such as various breathable fabrics, including polyurethane-coated ripstop nylons, polystyrene, or breathable membranes used in clothing such as stretched polytetrafluoroethylene, e-Vent®, and the like. For example, a "wicking" material may be employed that induces capillary action to draw moisture away from electrode 212, 312. In some embodiments, the heating element 214, 314 may be a resistor that is operable to generate heat by electrical current flow through it; although this is not to be understood as limiting. FIGS. 2 and 3 differ with respect to the heating elements 214, 314 contained therein.

FIG. 2 illustrates one example patch 200 configured with selected aspects of the present disclosure, which includes an electrode 212, a heating element 214 which may be constructed with materials such as metal, and power source 216. The electrode 212 may be an electrical conductor that is electrically coupled with, and powered by, the power source 216. In some embodiments, such as illustrated in FIG. 2, heating element 214 may be a metallic wire (e.g. a coiled wire) on a side of the electrode 212. In such embodiments, heating element 214 may come in direct contact with the skin surface 205 of the user, and/or may physically contact electrode 212.

FIG. 3 illustrates another patch 300 configured with selected aspects of the present disclosure, which also includes an electrode 312, a heating element 314 in the form of a metallic portion, and power source 316. The electrode 312 may be an electrical conductor that is electrically coupled with, and powered by, the power source 316. In some embodiments, such as illustrated in FIG. 3, the heating element 314 may be a flat metallic mesh disposed against the electrode 312. In such an embodiment, the heating element 314 may or may not be in direct contact with the skin surface 305, but instead may hover just above the skin surface 305 or may be placed against a surface of electrode 312 opposite skin surface 305. In the latter case, operating the heating element 314 may in turn heat the electrode 312. The embodiments illustrated in FIGS. 2 and 3 are not to be understood as limiting, as the heating element may be of any form known in the art. In other embodiments, the heating element may be solid state, for example in the form of a Peltier element.

A typical skin temperature for humans ranges between about 34 degrees Celsius and about 37 degrees Celsius, while temperatures lying outside this range may be noticeable to an individual. However, the temperature of the skin surface may be elevated to approximately 42 degrees Celsius before becoming uncomfortable. Sweat may be induced locally at the skin surface by increasing the temperature of the skin surface to about 38 degrees Celsius to about 39 degrees Celsius—below the point of becoming uncomfortable. In some instances, this sweat response may be induced within seconds.

Some degree of moisture may be beneficial in order to take an accurate biopotential measurement, such as an ECG measurement with an electrode 212, 312. Accordingly, heating element 214, 314 may be operable to generate heat (e.g. allowing a current to flow through the heating element) to cause the temperature of the skin surface 205, 305 underneath patch 200, 300 to rise enough to induce the formation of sweat 230, 330 (represented in broken line in FIGS. 2 and 3) without becoming uncomfortable for a wearer; therefore, balancing the need for accuracy and desirer for user comfort. The formation of sweat 230, 330 to the skin surface 205, 305 induced by the heating element 214, 314 may provide moisture to couple biopotential signals. The performance of the electrode 212, 312 may increase as the moisture level increases, which may be important in order to reduce contact impedance.

Once the ECG measurement is taken by the electrode 212, 312 the heating element 214, 314 may be deactivated. Once the heating element 214, 314 is deactivated the sweat 230, 340 (or the water component of the sweat) may diffuse, or be drawn, towards exterior surface 220, 320 of the patch 200, 300, which may be constructed of a porous or water permeable material. In some instances, the temperature gradient between the skin surface 205, 305 (e.g. about 34 degrees Celsius to about 37 degrees Celsius) and the atmospheric conditions outside of the patch 200, 300 (e.g. approximately 20 degrees Celsius for normal indoor conditions) may naturally drive a diffusion process (represented by the horizontal arrows in FIGS. 2 and 3) from the skin surface 205, 305 below the patch 200, 300 towards outside of the patch. In some instances, the humidity gradient between the skin surface (which may have high humidity) and the atmospheric air (which may have lower humidity) may further facilitate this diffusion process.

In an example, sweat 230, 330 generated close to the side of the electrode 212, 312 (for example, nearest exterior surface 220, 320 of the edge of the patch 200, 300) may evaporate within a few minutes, while sweat 230, 330 generated below the center of the electrode 212, 312 the evaporation process may take longer, for example about 10-20 minutes. In some instances, it may be desirable to take an ECG measurement every hour, which may allow the skin surface to dry between readings. In other instances, it may be desirable to take an ECG measurement more frequently (e.g. every 10 minutes), in which case at least some retained moisture may be reused.

Figure 4:
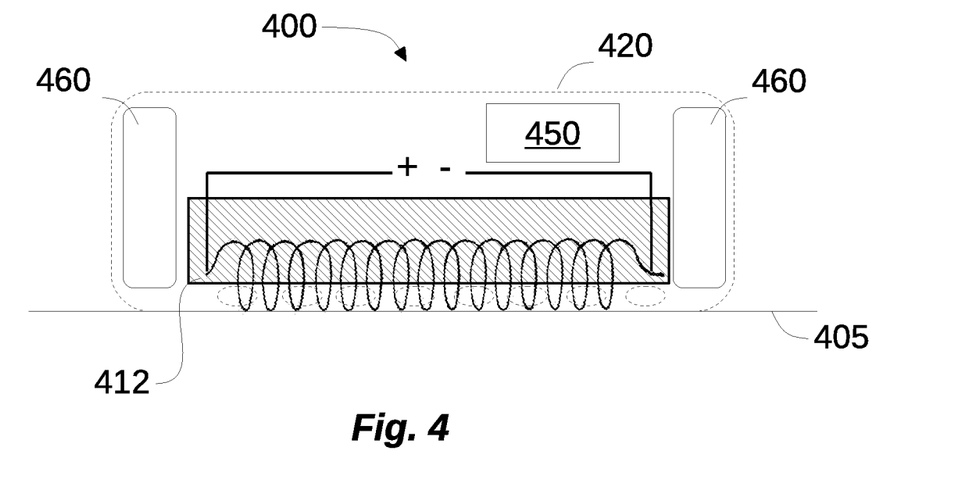
FIG. 4 illustrates a cross-sectional view of a self-regulating patch that is adhered to a user's skin surface according to some embodiments.

In some embodiments, such as illustrated in FIG. 4, the self-regulating sensor 400 may additionally include a drying material 460, such as silica gel, paper, or the like, to speed up the diffusion, evaporation, and/or drying process of the sweat from the skin surface 405. In some instances, this drying material 460 may be on one side of the electrode 412, while in other instances (such as illustrated in FIG. 4) the drying material 460 may be disposed on both sides of the electrode 412. In still other instances, the drying material may positioned as a ring around the electrode 412. Where such a drying material is incorporated into patch 400 it is also enveloped by the exterior surface 420. In some instances, the drying material 460 may be a phase changing material, such as various hydrogels used for drug delivery or a hydrophilic material (e.g. a hydrogels or silica particles). The drying material, in some instances, may not be able to be disposed between the electrode and the skin, as it could hamper the electrode-skin contact. However, in an embodiment where the drying material is also a conductive material, it may be possible to dispose the drying material between the electrode and the skin, for example as particles, a ring, or mesh so as not to inhibit the electrode-skin contact.

In other embodiments, a dynamic mechanical barrier, disposed similarly to the drying material of FIG. 4, may be used to transfer moisture. For example, the self-regulating patch may include such a dynamic mechanical barrier layer on each side of the electrode that enables moisture transfer through it (i.e. away from the skin) when the patch is in a comfort mode (described in detail herein); while the dynamic mechanical barrier may confine the moisture at the skin surface when an ECG measurement is desired. In some instances, this dynamic moisture barrier may include electroactive polymers arranged to create a porous architecture or to lift the patch. In other instances, the dynamic moisture barrier may be a temperature sensitive foam or a porous hydrophilic textile (e.g. Spandex) that may be stretched to elongate the pores of the textile.

Figure 5:
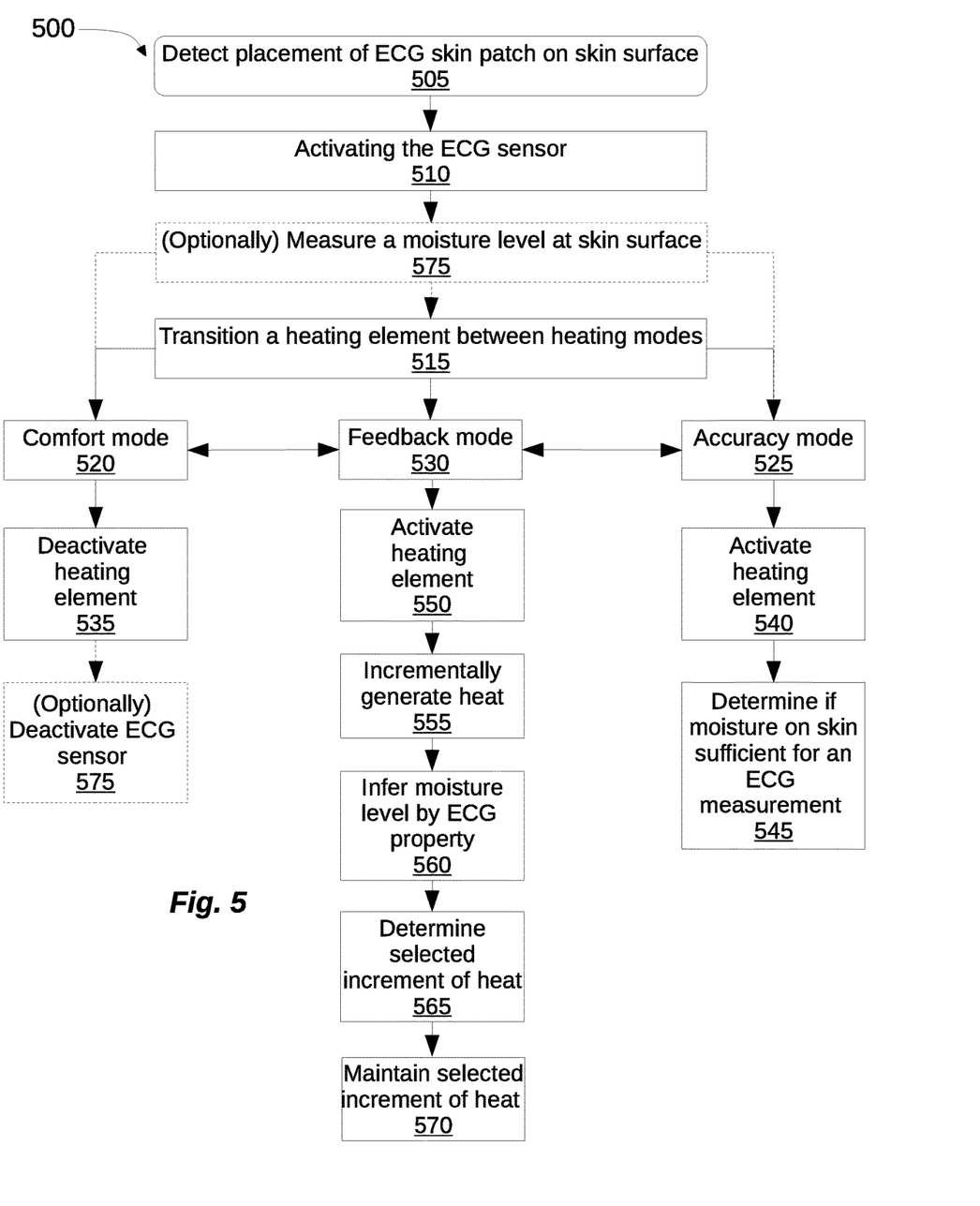
FIG. 5 is a flow chart of an exemplary method of regulating an ECG sensor patch according to some embodiments.

Referring now to FIG. 5, which illustrates a method for regulating a biopotential patch configured with selected aspects of the present disclosure, such as those illustrated in FIGS. 1-4. While the operations of FIG. 5 are described as being performed in association with an ECG sensor patch similar to those depicted in FIGS. 1-4, this is not meant to be limiting, and these operations may be performed with respect to any biopotential sensor patch.

As shown, the method 500 begins at block 505, where a logic (e.g., 250, 350, 450) may detect the placement of ECG sensor patch on the surface of a user's skin, e.g., by detecting an electrical coupling between the skin and the electrode. In some instances, the logic may then transmit a signal to any number of user devices (e.g. computer, tablet, smart phone, smart watch, etc.) indicating the patch is properly placed. At block 510, the logic may activate the ECG sensor to take one or more ECG measurements. At block 515, the logic may transition the sensor patch between a plurality of heating modes. This plurality of heating modes may include a comfort mode (block 520), an accuracy mode (525), and/or a feedback mode (530), each of which will be discussed in detail. In some embodiments, the operations of block 510 and 515 may be performed simultaneously and/or concurrently.

At block 520, the ECG patch may be transitioned into a comfort mode. When in comfort mode the heating element may be deactivated (block 535), allowing the skin to return to, or maintain, its natural temperature (e.g. approximately 34 degrees Celsius to 37 degrees Celsius). In some instances, deactivating the heating element may be accomplished by the creation of an open circuit within the heating element, e.g., by decoupling heating element 214, 314 from power source 216, 316. Optionally, at block 570, comfort mode may also include the deactivation of the ECG sensor, which may allow for conversation of power.

When the ECG sensor transitions into comfort mode (block 520), either from accuracy mode (block 525) or feedback mode (block 530), the moisture (e.g. sweat) generated by the user at the skin surface in response to the heating element being active may diffuse towards the exterior surface. This exterior surface may be constructed of a porous or water permeable material in order to wick the moisture away from the skin's surface. The temperature gradient between the skin surface (e.g. about 34 degrees Celsius to about 37 degrees Celsius) and the atmospheric conditions outside of the patch (e.g. approximately 20 degrees Celsius for normal indoor conditions) may also naturally drive a diffusion process from the skin surface below the patch towards outside of the patch when in comfort mode. In some instances, the humidity gradient may further facilitate this diffusion process.

When an ECG measurement is desired the ECG skin patch may be transitioned from a comfort mode (block 520) to either an accuracy mode (block 525) or a feedback mode (block 530). In some embodiments, there may be no distinct accuracy mode, and instead there may only be a comfort mode and a feedback mode. When in in accuracy mode, at block 540, the heating element may be activated, for example by closing a circuit between the heating element and the power source to cause electrical current to flow through the heating element. Activation of the heating element may generate heat, which may raise the temperature of the skin surface. For example, the heating element may need to reach about 38 degrees Celsius to about 42 degrees Celsius at the skin surface in order to induce sweating; however, this is not intended to be limiting as the precise temperature required to induce sweating in an individual may vary due to the architecture of the ECG skin patch (i.e. how much of the heating element is in contact with the skin surface), the individual user's heat tolerance levels, etc. In some instances, the temperature increase of the heating element required to achieve sweating may relatively small, therefore the target temperature may be reached relatively quickly (for example within a second) once the heating element is activated. The electrical power required to reach the target temperature (e.g. about 38 degrees Celsius to about 42 degrees Celsius) to induce sweating is relatively small, as such the power source may be the battery of the patch without significantly reducing the discharge time of the battery.

At block 545, the logic may utilize an ECG signal property generated by the ECG signal to infer a moisture level on the skin surface, where the moisture may be in response to the activation of the heating element. As a non-limiting example, the ECG signal property analyzed may be a signal-to-noise ratio. This inferred moisture level may be used, by the logic, to determine whether a measurement to be taken by the ECG sensor satisfies one or more quality or accuracy criterion or thresholds. This inferred moisture level may also be used, by the logic, to make determinations regarding the transition of the patch between the comfort mode and the accuracy mode. As mentioned previously, the performance of the ECG sensor increases as moisture increases, which reduces contact impedance.

In feedback mode, at block 530, the heating element may be activated, for example by closing the circuit and providing electrical current through the heating element. However, in contrast to accuracy mode (block 525), the activation of the heating element in feedback mode may be more finely tuned to cause the heating element to gradually and/or incrementally generate heat (block 555), which results in a gradual increase in the temperature of the skin surface. At block 560, the logic may utilize an ECG signal property generated by the ECG signal (e.g. a signal-to-noise ratio) to infer a moisture level on the skin surface. At block 565, a selected increment of heat is determined based on the moisture level inferred by the ECG signal property (in block 560). For example, in some instances, the selected increment may be the lowest temperature at which the moisture on the skin surface provides a quality ECG measurement. At block 570, the selected increment of heat may then be used as a set-point temperature that the logic maintains in order to balance the desired accuracy of the ECG sensor measurement and the user's comfort.

While described herein as capable of transitioning between modes, the self-regulating patch is not so limited. In some instances, it may be desirable for the patch to only include a single mode. For example, in some embodiments, the patch may only include what is described herein as the feedback mode. In such an embodiment, similar to what has been previously described herein, a moisture level (e.g. the amount of sweat) on a user's skin surface may be inferred based on a properties of the ECG signal and this inference is then used to determine a selected heating increment (e.g. temperature or range of temperature), which could an increment of no heat. Maintaining this selected temperature (or range of temperatures) may allow for both a quality ECG measurement to be taken and the user to be comfortable and not overheated at the location of the patch.

In some instances, in order to manage battery efficiency, this set-point temperature (i.e. the selected increment of heat maintained by the patch) may be reduced if the ECG sensor is placed in a low-power mode. It may also be possible in some instances to exploit that operating the various electronics in the ECG sensor patch results in the dissipation of heat by placing various electronics (e.g. the logic or controller, transmitter, etc.) near the skin. Alternatively, the heat from the various electronics may be guided via a heat sink (for example, the heating element) towards the skin.

In some instances, the ECG sensor may additionally or alternatively include a moisture sensor, such as ultra-small humidity sensors similar to those used in other commercial applications (e.g. headphones, helmets, etc.). At optional block 575, a measurement of moisture levels on the skin surface may be taken by a logic, and this data may be used to facilitate the transition between the comfort mode and accuracy mode or feedback mode. Alternatively, the moisture level on the skin surface and around the electrode may be inferred from a galvanic skin response sensor embedded in the patch. Such a galvanic skin response sensor may also provide a direct link to skin conductance, as well as the sweat gland activity.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. A self-regulating patch for adhering to a skin surface, comprising:
    a heating element that is operable to generate heat, wherein the heat causes formation of sweat at the skin surface;
    an electrocardiogram ("ECG") sensor;
    an exterior surface enveloping the heating element and the ECG sensor, wherein the exterior surface is constructed of a material that draws moisture away from the ECG sensor;
    a logic to:
        activate the ECG sensor;
        utilize one or more properties of an ECG signal generated by the ECG sensor to infer a moisture level on the skin surface; and
        transition the self-regulating patch between a plurality of modes, including a comfort mode and an accuracy mode;
        wherein the logic transitions the self-regulating patch between the comfort mode and the accuracy mode based on the inferred moisture level.

2. The self-regulating patch of claim 1, wherein the one or more properties of the ECG signal include a signal-to-noise ratio.

3. The self-regulating patch of claim 1, wherein the accuracy mode comprises a feedback mode, wherein the heating element is further operable to generate heat in increments, and wherein the logic operates the heating element to generate a selected increment of heat, wherein the increment of heat is selected based on the inferred moisture level.

4. The self-regulating patch of claim 1, wherein the heating element comprises a metallic mesh disposed adjacent an electrode of the ECG sensor.

5. The self-regulating patch of claim 1, wherein the heating element comprises a metallic wire disposed on an electrode of the ECG sensor.

6. The self-regulating patch of claim 1, further comprising a moisture sensor to facilitate the transition between the plurality of heating modes.

7. The self-regulating patch of claim 1, further comprising a drying material disposed adjacent an electrode of the ECG sensor.

8. The self-regulating patch of claim 1, wherein the heating element reaches a temperature between about 38 degrees Celsius and about 42 degrees Celsius at the skin surface when active.

9. The self-regulating patch of claim 1, wherein the comfort mode the heating element is inactive, and wherein in the accuracy mode the heating element is active.

10. A self-regulating patch for adhering to a skin surface, comprising:
    a heating element operable to generate heat in increments, wherein the heat causes formation of sweat at the skin surface;
    an electrocardiogram ("ECG") sensor;
    an exterior surface enveloping the heating element and the ECG sensor, wherein the exterior surface is constructed of a material that draws moisture away from the ECG sensor;
    a logic to:
        activate the ECG sensor;
        utilize one or more properties of an ECG signal generated by the ECG sensor to infer a moisture level on the skin surface;
        determine a selected increment of heat based on the inferred moisture level; and
        operate the heating element to generate the selected increment of heat.

11. The self-regulating patch of claim 10, wherein the one or more properties of the signal generated by the ECG sensor includes a signal-to-noise ratio.

12. The self-regulating patch of claim 10, wherein the heating element takes the form of a metallic wire positioned adjacent an electrode of the ECG sensor.

13. The self-regulating patch of claim 10, wherein the heating element takes the form of a metallic mesh positioned against an electrode of the biopotential sensor.

14. A method of regulating a biopotential skin patch adhered to a skin surface of a subject in order to balance comfort and moisture levels, wherein the biopotential skin patch comprises a heating element operable to generate heat in increments to cause formation of sweat at the skin surface, an electrocardiogram ("ECG") sensor, an exterior surface that draws moisture away from the ECG sensor and that envelops the heating element and the ECG sensor, and a logic operably coupled with the heating element and the ECG sensor, the method comprising:
  activating, by the logic, the ECG sensor to measure electrical activity generated by one or more physiological processes of the subject;
  inferring, by the logic, a moisture level based on one or more properties of a signal generated by the ECG sensor;
  determining, by the logic, a selected increment or selected reduction of heat based on the inferred moisture level; and
  operating, by the logic, the heating element in a manner to cause the selected increment or selected reduction of heat.

15. The method of claim 14, wherein the heating element takes the form of a metallic mesh positioned against an electrode of the biopotential sensor.

16. The method of claim 14, wherein the one or more properties of the signal generated by the ECG sensor includes a signal-to-noise ratio.

17. The method of claim 14, wherein the heating element takes the form of a metallic wire positioned adjacent an electrode of the ECG sensor.

18. The method of claim 14, wherein the biopotential skin patch further comprises a moisture sensor, and wherein the moisture level is further inferred based on a moisture sensor signal.

19. The method of claim 14, wherein the biopotential skin patch further comprises a drying material disposed adjacent an electrode of the ECG sensor.

20. The method of claim 14, wherein the heating element reaches a temperature between about 38 degrees Celsius and about 42 degrees Celsius at the skin surface.

* * * * *